United States Patent
Tarnow et al.

(10) Patent No.: US 11,938,169 B2
(45) Date of Patent: Mar. 26, 2024

(54) GM-CSF FOR TREATING REFRACTORY NON-TUBERCULOUS MYCOBACTERIA INFECTIONS

(71) Applicants: DRUGRECURE APS, Hørsholm (DK); MAYO FOUNDATION FOR MEDICAL EDUCATION AND RESEARCH, Rochester, MN (US)

(72) Inventors: Inge Tarnow, Hørsholm (DK); Cecilia Ganslandt, Hørsholm (DK); Mark E. Wylam, Rochester, MN (US)

(73) Assignees: drugrecure APS, Hørsholm (DK); Mayo Foundation for Medical Education and Research, Rochester, MN (US)

( * ) Notice: Subject to any disclaimer, the term of this patent is extended or adjusted under 35 U.S.C. 154(b) by 205 days.

(21) Appl. No.: 16/755,178

(22) PCT Filed: Oct. 16, 2018

(86) PCT No.: PCT/EP2018/078214
§ 371 (c)(1),
(2) Date: Apr. 10, 2020

(87) PCT Pub. No.: WO2019/076883
PCT Pub. Date: Apr. 25, 2019

(65) Prior Publication Data
US 2020/0237869 A1 Jul. 30, 2020

Related U.S. Application Data

(60) Provisional application No. 62/572,711, filed on Oct. 16, 2017.

(30) Foreign Application Priority Data

Oct. 27, 2017 (EP) .................................... 17198938

(51) Int. Cl.
A61K 38/19 (2006.01)
A61P 11/00 (2006.01)
A61K 9/00 (2006.01)
A61K 45/06 (2006.01)

(52) U.S. Cl.
CPC ............ *A61K 38/193* (2013.01); *A61P 11/00* (2018.01); *A61K 9/007* (2013.01); *A61K 45/06* (2013.01)

(58) Field of Classification Search
None
See application file for complete search history.

(56) References Cited

U.S. PATENT DOCUMENTS

| | | |
|---|---|---|
| 4,235,871 A | 11/1980 | Papahadjopoulos et al. |
| 4,501,728 A | 2/1985 | Geho et al. |
| 4,837,028 A | 6/1989 | Allen |
| 5,229,496 A | 7/1993 | Deeley et al. |
| 5,391,485 A | 2/1995 | Deeley et al. |
| 5,393,870 A | 2/1995 | Deeley et al. |
| 2010/0015217 A1 | 1/2010 | Fiala |
| 2017/0165374 A1* | 6/2017 | Perkins ................. A61P 11/08 |
| 2019/0160086 A1 | 5/2019 | Eagle et al. |

FOREIGN PATENT DOCUMENTS

| | | |
|---|---|---|
| JP | 2010-508365 A | 3/2010 |
| JP | 2017-515913 A | 6/2017 |
| WO | 2008/052567 A2 | 5/2008 |
| WO | 2015/132392 A1 | 9/2015 |
| WO | 2015/175939 A1 | 11/2015 |

OTHER PUBLICATIONS

Nessar et al. (2012, J. Antimicrob. Chemother. 67:810-818).*
Kwon et al. (2016, J. Korean Med. Sci. 31:649-659).*
Armitage et al. (1998, Blood 98(12):4491-4508).*
Altemeier et al., "Hyperoxia in the intensive care unit: why more is not always better", Curr Opin Crit Care, Feb. 2007, 13(1), 73-78.
Baleeiro et al., CSF and the impaired pulmonary innate immune response following hyperoxic stress, Am. J. Physiol Lung Cell Mol Physiol., Dec. 2006, 291(6), L1246-55.
Chen et al., Role of granulocyte macrophage colony-stimulating factor in host defense against pulmonary Cryptococcus neoformans infection during murine allergic bronchopulmonary mycosis, Am. J. Pathol., Mar. 2007, 170(3), 1028-1040.
De Silva, T.T. et al., "The use of adjuvant granulocyte-macrophage colony-stimulating factos in HIV-related disseminated atypical mycobacterial infection", Journal of Infection, 2007, 54, e207-e210.
Francisco-Cruz, A. et al., "Efficacy of gene-therapy based on adenovirus encoding granulocyte-macrophage colony-stimulating factor in drug-sensitive and drug-resistant experimental pulmonary tuberculosis", Tuberculosis 100, 2016, 5-14.
Griffith et al., An official ATS/IDSA statement: Diagnosis, Treatment and Prevention of Nontuberculous mycobacterial diseases, Am. J. Respir. Crit. Care Med., 2007, 175(4), 367-416.
Johnson, M.M. and Odell, J.A., "Nontuberculous mycobacterial pulmonary infections", J Thorac Dis, 2014; 6(3):210-220.
Nambiar, J.K. et al., "Modulation of pulmonary DC function by vaccine-encoded GM-CSF enhances protective immunity against *Mycobacterium tuberculosis* infection", Eur. J. Immunol. 2010. 40: 153-161.
Quittner et al., Quality of Life Questionnaire-Bronchiectasis: final psychometric analyses and determination of minimal important difference scores, Thorax, 2015, 70(1), 12-20.
Scott, J.P. et al., "Inhaled Granulocyte-Macrophage Colony Stimulating Factor for Mycobacterium Abscessus in Cystic Fibrosis", European Respiratory Society. Published on Feb. 1, 2018.
(Continued)

*Primary Examiner* — Elizabeth C. Kemmerer
(74) *Attorney, Agent, or Firm* — BakerHostetler

(57) ABSTRACT

The present invention relates to methods of treating subjects suffering from a pulmonary NTM infection refractory to treatment, for example to antibiotic treatment.

23 Claims, 1 Drawing Sheet
Specification includes a Sequence Listing.

(56) References Cited

OTHER PUBLICATIONS

Suzuki, K. et al., "Recombinant granulocyte-macrophage colony-stimulating factor (GM-CSF) or tumour factor-alpha (TNF-a) activate human alveolar macrophages to inhibit growth of *Myobacterium avium* complex", Clin Exp Immunol, 1994; 98: 169-173.

Szoka et al., Comparative properties and methods of preparation of Lipid vesicles (Liposomes), Ann. Rev. Biophys. Bioeng., 1980, 9, 467.

Trapnell BC and Whitsett JA, "GM-CSF regulates pulmonary surfactant homeostasis and alveolar macrophage-mediated innate host defense", Annu. Rev. Physiol., 2002, 64, 775-802.

Wong et al., Science, "Human GM-CSF: Molecular Cloning of the Complementary DNA and Purification of the Natural and Recombinant Proteins", 1985, vol. 228, pp. 810-815.

Zobywalski et al., generation of clinical grade dendritic cells with capacity to produce biologically active IL-12p70, J. Transl. Med., Apr. 12, 2007, 5, 18.

Gupta et al., "Potential of *Mycobacterium vanbaalenii* as a model organism to study drug transporters of *Mycobacter tuberculosis, Mycobacterium marinum* and *Mycobacterium ulcerans:* Homology analysis of *M. tuberculosis* drug transporters among mycobacterial species", Infection Genetics and Evolution, 2012, 853-856.

Zhang et al., "Immunotherapy using IL-2 and GM-CSF is a potential treatment for multidrug-resistant *Mycobacterium tuberculosis*", vol. 55, No. 9, 2012, 800-806.

DaCosta et al., Outcomes associated with antibiotic regimens for treatment of *Mycobacterium abscessus* in cystic fibrosis patients, Journal of Cystic Fibrosis, 16, 2017, pp. 483-487.

Vinnard et al., "Assessing Response to Therapy for Nontuberculous Mycobacterial Lung Disease: Quo Vadis?", Nov. 2018, vol. 9, Article 2813, pp. 1-8.

\* cited by examiner

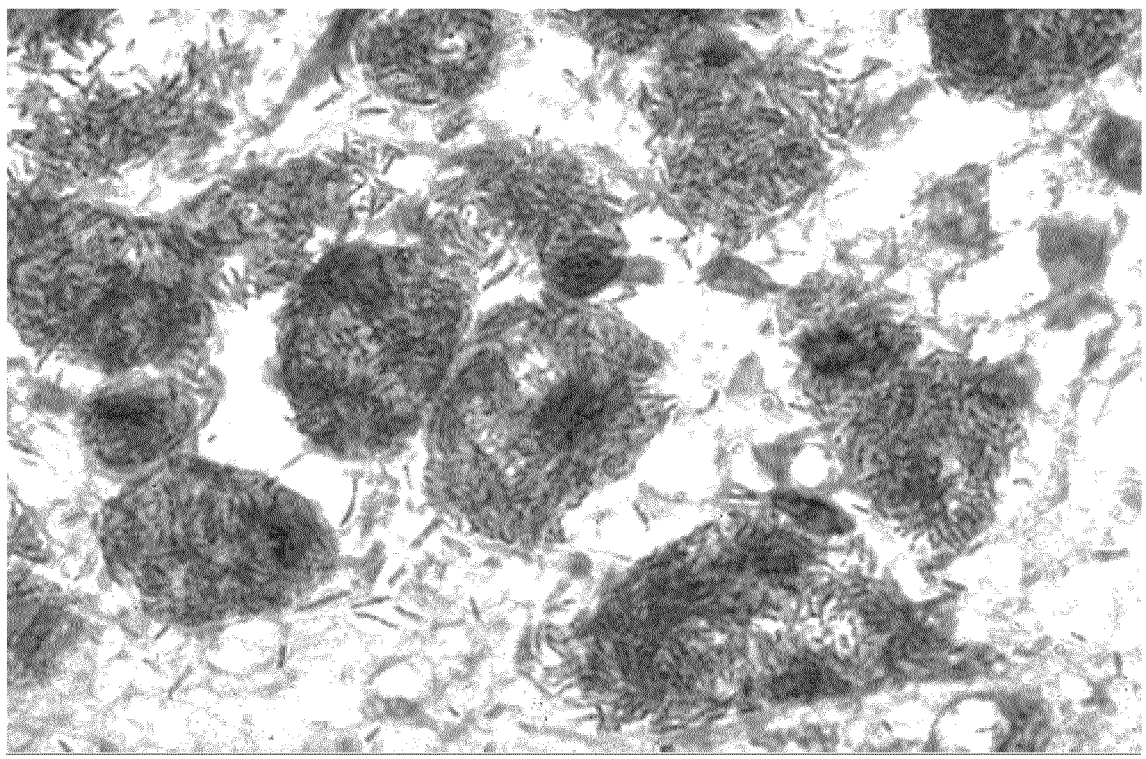

GM-CSF FOR TREATING REFRACTORY NON-TUBERCULOUS MYCOBACTERIA INFECTIONS

CROSS-REFERENCE TO RELATED APPLICATIONS

This application is the National Stage of International Patent Application No. PCT/EP2018/078214, filed Oct. 16, 2018, which claims the benefit of U.S. Application No. 62/572,711, filed Oct. 16, 2017 and EP Application Number 17198938.7, filed Oct. 27, 2017, the disclosures of which are incorporated herein by reference in their entireties.

SEQUENCE LISTING

The instant application contains a Sequence Listing which is being submitted herewith electronically in ASCII format and is hereby incorporated by reference in its entirety.

TECHNICAL FIELD

The present invention relates to methods of treating subjects suffering from a pulmonary NTM infection refractory to treatment, for example antibiotic treatment.

BACKGROUND

Pulmonary disease due to non-tuberculous mycobacteria (NTM) is a burgeoning problem in the USA and most western countries. NTMs cause progressive lung destruction resulting in a variety of symptoms including cough, breathlessness and weight loss.

NTMs are ubiquitous in the soil and water in our environment. Sampling data suggests that the amount of NTM is increasing, especially in water sources, for reasons that are not entirely clear. Initially coming to prominence as a systemic infection in the setting of advance human immunodeficiency virus (HIV) disease, NTM are now recognized to be a major cause of chronic lung disease, and especially bronchiectasis, in apparently immunocompetent people. Since the 1990's there has been a dramatic increase in the number of patients diagnosed with lung disease due to NTM. Over the same period NTM have also become a significant problem in patients with cystic fibrosis. Reflecting USA experience, in Queensland, Australia, where NTM is a reportable disease, the incidence increased by 45% between 1995 and 2005. This increase has been attributed to 1) improved diagnostic techniques, 2) increased physician recognition of NTM causing disease, 3) the aging population as this is particularly a disease occurring in older age groups and 4) a real increase in the prevalence of the disease possibly due to greater environmental exposure.

Current estimates of the prevalence of NTM disease in the USA vary from 3 to 7 cases per 100,000 people, with substantial variation between different regions. As disease frequency increases markedly with age, the prevalence in the over 65 age group is reported as being ~50 per 100,000. Similar prevalence rates are reported in most western countries. It is likely that these prevalence rates are a significant underestimate. Consistent with under recognition of disease in the USA, with compulsory reporting of NTM disease in Queensland, the prevalence of NTM disease in the general population was 15.1 per 100,000 in 2010.

Treatment of NTM infection is difficult, typically requiring at least 3 antibiotics for a minimum of 18 months. This treatment regime is poorly tolerated with up to ¼ of patients not able to tolerate treatment with a large number of side effects including nausea, vomiting, diarrhea, peripheral neuropathy, loss of vision and hearing, liver failure, kidney failure and bone marrow suppression. In those who do tolerate treatment the best reported success rates are 70-80%, so the overall success rate of therapy is around 50%. Even in those with apparent successful antibiotic treatment, nearly 50% have reacquired or reactivated disease within 3 years. New methods of treatment are needed.

SUMMARY

Herein is provided a method of treating a pulmonary NTM infection refractory to antibiotic treatment in a subject in need thereof, comprising administering to the subject via pulmonary administration an effective amount of granulocyte-macrophage colony stimulating factor (GM-CSF) or a functional homologue thereof.

Also provided is a kit of parts comprising dose units of GM-CSF for an inhalator and instructions for use, for use in a method of treating a pulmonary NTM infection refractory to antibiotic treatment as disclosed herein.

DESCRIPTION OF THE DRAWINGS

FIG. 1 Macrophages invaded by non-tuberculous bacteria, visualised by acid-fast stain.

DETAILED DESCRIPTION

The invention is as defined in the claims.

Definitions

Refractory: in the present context, the term refractory when applied to an NTM disease or infection refers to an NTM disease or infection which is refractory to treatment, e.g. treatment by antibiotics. This can be due to inherent resistance of the NTM to be treated, or it can be a consequence of the patient being intolerant to treatment. In other words, a refractory NTM disease or infection refers to an NTM disease or infection which is resistant to treatment.

Non-Tuberculous Mycobacteria

Mycobacteria are a family of small, rod-shaped bacilli that can be classified into 3 main groups for the purpose of diagnosis and treatment:

*Mycobacterium tuberculosis* complex which can cause tuberculosis: *M. tuberculosis, M. bovis, M. africanum, M. microti* and *M. canetti;*

*M. leprae* and *M. lepromatosis* which cause Hansen's disease or leprosy;

Nontuberculous mycobacteria (NTM) are all the other mycobacteria which can cause pulmonary disease resembling tuberculosis, lymphadenitis, skin disease, or disseminated disease.

Nontuberculous mycobacteria (NTM), also known as environmental mycobacteria, atypical mycobacteria and mycobacteria other than tuberculosis (MOTT), are mycobacteria which do not cause tuberculosis or leprosy. NTM do cause pulmonary diseases that resemble tuberculosis. The term mycobacteriosis refers to any of these illnesses, and is usually meant to exclude tuberculosis.

Herein is disclosed that administration of an effective amount of GM-CSF or a functional homologue thereof via intratracheal, intrabronchial or bronchio-alveolar administration is particularly useful in alleviating symptoms and/or treating subjects suffering from infections by non-tuberculous mycobacteria (NTM), particularly those infections which are caused by NTM which are refractory to treatment such as antibiotic treatment.

The Runyon classification is usually employed to sort NTM in one of the following four groups:
i. Photochromogens, which develop pigments in or after being exposed to light. Examples include *M. kansasii, M. simiae* and *M. marinum*.
ii. Scotochromogens, which become pigmented in darkness. Examples include *M. scrofulaceum* and *M. szulgai*.
iii. Non-chromogens, which includes a group of prevalent opportunistic pathogens called *M. avium* complex (MAC). Other examples are *M. ulcerans, M. xenopi, M. malmoense, M. terrae, M. haemophilum* and *M. genavense*.
iv. Rapid growers include four well recognized pathogenic rapidly growing non-chromogenic species: *M. chelonae, M. abscessus, M. fortuitum* and *M. peregrinum*. Other examples cause disease rarely, such as *M. smegmatis* and *M. flavescens*.

Although over 160 species of NTM cause human disease, the most common the USA are *M. avium* and *M. intracellulare*, and in a few regions *M. kansasii. M. abscessus* is also a problem in the USA as it is much more aggressive infection than other NTM with worse patient outcomes and requires intravenous and oral therapy. While NTM are not near as contagious as tuberculosis, they are transmissible from human to human, and in the case of *M. abscessus* this may be the major route of acquisition.

In the context of the present disclosure, the NTM may belong to any of the above four groups. Thus the NTM which is refractory to treatment, such as antibiotic treatment, may be a photochromogen, a scotochromogen a non-chromogen or a rapid grower.

In one embodiment, the NTM is a photochromogen, such as *Mycobacterium kansasii, Mycobacterium simiae* or *Mycobacterium marinum*. In another embodiment, the NTM is a scotochromogen such as *Mycobacterium scrofulaceum* or *Mycobacterium szulgai*. In another embodiment, the NTM is a non-chromogen such as *Mycobacterium avium* complex (MAC), *Mycobacterium ulcerans, Mycobacterium xenopi, Mycobacterium malmoense, Mycobacterium terrae, Mycobacterium haemophilum* or *Mycobacterium genavense*. In another embodiment, the NTM is a rapid grower such as *Mycobacterium chelonae, Mycobacterium abscessus, Mycobacterium fortuitum, Mycobacterium peregrinum, Mycobacterium smegmatis* or *M. flavescens*. In preferred embodiments, the NTM is selected from the group consisting of *M. abscessus*, MAC, *M. fortuitum* and *M. kansasii*. In even preferred embodiments, the NTM is *M. abscessus* or MAC.

Subjects in Need of Treatment

The methods disclosed herein are particularly useful for treating NTM infections which are refractory to treatment, such as antibiotic treatment. An NTM infection is refractory to treatment when the treatment has no effect and cannot resorb the infection, or when the subject having an infection cannot tolerate treatment. For example, an NTM infection is refractory to antibiotic treatment when the antibiotic treatment has no effect and cannot resorb the infection, or when the subject having an infection cannot tolerate antibiotic treatment.

In some embodiments, the subjects in need of treatment have been diagnosed with NTM and have already received a treatment, such as an antibiotic treatment, as is known in the art.

The person of skill in the art knows how to diagnose an NTM infection. NTM infections are sometimes diagnosed late because the symptoms are vague and not always recognised by the infected subjects. Typical symptoms are weight loss and fatigue.

The minimum evaluation of a patient suspected of NTM disease typically includes:
(1) A chest radiograph or, in the absence of cavitation, chest high-resolution computed tomography (HRCT) scan;
(2) Three or more sputum specimens for acid-fast bacilli (AFB) analysis;
(3) Exclusion of other disorders, such as tuberculosis.

Although these criteria fit best with MAC, *M. abscessus* and *M. kansasii*, it is thought, without being bound by theory, that they are also useful for diagnosing other NTM diseases.

Diagnosis is typically performed by determining the mycobacterial load in the lungs of a subject, for example by multiple sputum cultures and determination of the presence of NTMs, or by bronchial lavage NTM culture or lung biopsy, or a combination thereof. The NTM cultures, e.g. sputum cultures or bronchoalveolar lavage fluid cultures, may be stained using a staining which is NTM-specific. Alternatively or additionally, quantitative PCR may be performed to detect the presence of NTM in the cultures.

Other tools may be used when the presence of an NTM infection is suspected. One of them is the quality of life questionnaire bronchiectasis (QOL-B), as described in Quittner et al., 2015. The QOL-B is a self-administered patient-reported outcome measure, and while it has been developed for assessing functioning of non-CF bronchiectasis patients in their daily lives, it can be used also for assessing NTM infections which often accompany bronchiectasis. The QOL-B includes 37 items on 8 scales (respiratory symptoms, physical, role, emotional and social functioning, vitality, health perceptions and treatment burden). The QOL-B questionnaire may be particularly useful for assessing the efficacy of a treatment, by measuring potential improvement over the duration of treatment.

A review of useful diagnostic methods is provided in Griffith et al., 2007, which also describes how to culture NTMs.

The nature of the treatment, e.g. the antibiotic treatment, administered to subjects diagnosed with an NTM infection may depend upon the nature of the NTM. Griffith et al., 2007, provides an overview of existing methods for treating various NTM infections.

Subjects suffering from MAC infections may typically receive macrolides treatment, in particular clarithromycin, and azalides such as azithromycin, and ethambutol. These may be combined with companion drugs such as a rifamycin and optionally an injectable aminoglycoside. The dosages may vary depending on the severity of the disease.

Subjects suffering from *M. abscessus* infections may typically involve suppressive therapy, e.g. periodic parenteral antibiotic therapy or oral macrolide therapy. Ethambutol, rifampicin, azithromycin, clofazimine, linezolid, amikacin, cefoxitin, pyrazinamide and isoniazid are antibiotics which are commonly used for treating such infections. Non-antibiotic drugs such as lumicaftor/ivacaftor may also be used.

Subjects suffering from *M. kansasii* infections may typically receive rifampicin, isoniazid, ethambutol, ethionamide, streptomycin or clarithromycin or combinations thereof.

The subjects suffering from an NTM infection which is refractory to treatment such as antibiotic treatment may thus already be receiving any of the treatments which are known in the art, including, but not limited to, the treatments mentioned above. In some embodiments, the infection refractory to treatment such as antibiotic treatment has been present for at least three months, such as at least four months, such as at least five months, such as at least six months or more, such as one year or more, such as eighteen months or more. The infection is refractory where no improvement is observed over the period of treatment such as antibiotic treatment, by any of the diagnostic or assessment methods known in the art, including the methods described herein.

The original treatment, in particular the antibiotic treatment, may in some embodiments be discontinued when the subject starts receiving pulmonary administration of GM-CSF. In other embodiments, the treatment, in particular the antibiotic treatment, is not discontinued.

Any of the diagnostic methods known in the art, including the methods mentioned herein above, may also be used to assess improvement over time after pulmonary administration of GM-CSF, e.g. by inhalation, has begun.

Some patients may be prone to side-effects when receiving treatment, in particular antibiotic treatment. The present methods can also be used to treat such patients. Since these patients cannot tolerate treatment, the infection they suffer from can also be considered refractory.

Common side-effects are described herein. Patients being administered ethambutol may develop optic neuritis, i.e. they may lose or partly lose the ability to discriminate red and green and lose visual acuity. In such cases, it is recommended to discontinue drug administration immediately, and monitor development of optic neuritis.

Patients receiving rifampicin and rifabutin may experience an orange discoloration of secretions and urine as well as staining of soft contact lenses. Other side-effects include gastrointestinal disturbances (nausea, vomiting), hypersensitivity (fever, rash), hepatis, increased hepatic metabolism of numerous agents (for example birth control pills, ketoconazole, quinidine, prednisone, oral hypoglycemics, digitalis, methadone, warfarin, clarithromycin and protease inhibitors), flu-like syndrome, thrombocytopenia and/or renal failure.

Patients receiving azithromycin and clarithromycin may experience gastrointestinal disturbances (nausea, vomiting, diarrhea), decreased hearing, or develop hepatitis.

Administration of clarithromycin may be followed by inhibited hepatic metabolism of several agents, including rifabutin and some protease inhibitors.

Numerous side-effects can also be caused by other drugs commonly used for therapy or prophylaxis of NTM, as detailed in table 6 of Griffith et al., 2007. Patients experiencing any of said side-effects may prefer to discontinue treatment if they become too uncomfortable. For such patients, inhalation of GM-CSF as disclosed herein is thus also relevant.

GM-CSF

Colony-stimulating factors are glycoproteins that stimulate the growth of hematopoietic progenitors and enhance the functional activity of mature effector cells Human mature GM-CSF (SEQ ID NO: 1) is a monomeric protein of 127 amino acids with several potential glycosylation sites. It is generated from a pre-protein precursor with 144 amino acids. The variable degree of glycosylation results in a molecular weight range between 14 kDa and 35 kDa. Non-glycosylated and glycosylated GM-CSF show similar activity in vitro. There are two known sequence variants of GM-CSF. In one embodiment, GM-CSF as used herein is mature GM-CSF with an N-terminal start methionine.

```
>sp|P04141|18-144
                                        SEQ ID NO: 1
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQE

GM-CSF precursor. Signal peptide is shown in bold.
                                        SEQ ID NO: 2
>sp|P04141|CSF2_HUMAN Granulocyte-macrophage
colony-stimulating factor
MWLQSLLLLGTVACSISAPARSPSPSTQPWEHVNAIQEARRLLNLSRDTA

AEMNETVEVISEMFDLQEPTCLQTRLELYKQGLRGSLTKLKGPLTMMASH

YKQHCPPTPETSCATQIITFESFKENLKDFLLVIPFDCWEPVQE
```

GM-CSF exerts its biological activity by binding to its receptor. Formation of the GM-CSF trimeric receptor complex leads to the activation of complex signaling cascades.

Apart from its hemopoietic growth and differentiation stimulating activity, GM-CSF functions especially as a proinflammatory cytokine. Macrophages, e.g. alveolar macrophages type I & II and monocytes as well as neutrophils and eosinophils become activated by GM-CSF, resulting in the release of other cytokines and chemokines, matrix degrading proteases, increased HLA expression and increased expression of cell adhesion molecules or receptors for CC-chemokines which in turn, leads to increased chemotaxis of inflammatory cells into inflamed tissue.

Over the past several decades, a number of studies have contributed significantly to the understanding of the pharmacology of GM-CSF with respect to alveolar macrophage ontogeny, maintenance, and function, and to pulmonary alveolar surfactant homeostasis, alveolar stability, lung function, and lung host defense. For example, pulmonary GM-CSF is required for the terminal differentiation of alveolar macrophages and acquisition of numerous functions including expression of multiple receptor, non-specific and receptor-mediated endocytosis and phagocytosis, pathogen-stimulated proinflammatory cytokine response, pulmonary neutrophil recruitment during infection, clearance of bacterial, viruses, mycobacteria, and other pathogens, surfactant clearance. Pulmonary GM-CSF is also one of the endogenous alveolar factors required for phenotypic determination of the alveolar macrophage and for determining the size of the alveolar macrophage population (via a reciprocal feedback loop). Administration of inhaled rhGM-CSF to patients with aPAP has been reported to improve alveolar macrophage functions relevant to the therapeutic mechanism of action including surfactant clearance capacity as well as host defense functions. In addition, the effect of GM-CSF has been evaluated in inhalation studies in animal models where GM-CSF has been shown to reduce alveolar proteinosis and to improve the innate immune system response in the lung.

Several forms of recombinant human GM-CSF exist: molgramostim is rhGM-CSF produced in *Escherichia coli*; sargramostim refers to rhGM-CSF expressed in *Saccharomyces cerevisiae*; and regramostim refers to rhGM-CSF derived from Chinese hamster ovary cells (CHO). Since they are produced in eukaryotic systems, sargramostim and regramostim are glycosylated, while molgramostim is not.

No significant differences between the effects of molgramostim and sargramostim have been identified so far. The methods of treatment disclosed herein can thus be based on the pulmonary administration of any of the above forms of GM-CSF, namely sargramostim, molgramostim and regramostim. In one embodiment, GM-CSF is molgramostim.

Functional Homologues

Methods of treatment as disclosed herein may in some embodiments comprise administration of a functional homologue of GM-CSF.

A functional homologue of GM-CSF is a polypeptide having at least 80% sequence identity with SEQ ID NO. 1 and has one or more GM-CSF functions, such as the stimulation of the growth and differentiation of hematopoietic precursor cells from various lineages, including granulocytes, macrophages, eosinophils and erythrocytes.

GM-CSF regulates multiple functions of alveolar macrophages (AM). GM-CSF stimulation of AM has been documented to enhance alveolar macrophages selectively respond to noxious ingestants, i.e., stimulation of inflammation during bacterial phagocytosis, non-noxious ingestants are generally mollified, i.e., anti-inflammatory responses during phagocytosis of apoptotic cells. Other AM functions are also enhanced by GM-CSF stimulation with subsequent proliferation, differentiation, accumulation and activation. These GM-CSF effects also encompasses cell adhesion, improved chemotaxis, Fc-receptor expression, complement- and antibody-mediated phagocytosis, oxidative metabolism, intracellular killing of bacteria, fungi, protozoa, and viruses, cytokine signaling, and antigen presentation. Moreover, GM-CSF enhances defects in AM cell adhesion, pathogen associated molecular pattern receptors, like Toll-like receptors and TLR trans-membranous signaling, surfactant protein and lipid uptake and degradation (Trapnell B C and Whitsett J A. 2002).

GM-CSF also interacts with the AM's recognition receptors, the so-called toll like receptors (TLR). GM-CSF is important in the pulmonary host defense in pneumonia due to its interaction with the TLR's participation in the host defense resulting in enhanced clearance of the causative microorganism (Chen et al. 2007). Lung has its own innate GM-CSF production, which is reduced in pneumonia and hyperoxia, in relation to high $O_2$ exposure as seen in, e.g. ventilator associated pneumonia (VAP) contributing impairment of host defense secondary to apoptosis with poor response to infections. The hyperoxic injury seems to be counteracted by activation of alveolar macrophages with GM-CSF (Altemeier et al. 2007 & Baleeiro et al. 2006) with subsequent clearance of *P. aeruginosa* via expression of the TLR signaling pathway (Baleeiro et al., 2006).

Finally GM-CSF produces in-vitro conversion of AM into immature dendritic cells (DC), which may further be matured with specific agents in respect to activate the homing of matured DC's to a specified receptor or target (Zobywalski et al. 2007).

Preferably, evolutionary conservation between GM-CSF of different closely related species, e.g. assessed by sequence alignment, can be used to pinpoint the degree of evolutionary pressure on individual residues. Preferably, GM-CSF sequences are compared between species where GM-CSF function is conserved, for example but not limited to mammals including rodents, monkeys and apes. Residues under high selective pressure are more likely to represent essential amino acids that cannot easily be substituted than residues that change between species. It is evident from the above that a reasonable number of modifications or alterations of the human GM-CSF sequence does not interfere with the activity of the GM-CSF molecule according to the invention. Such GM-CSF molecules are herein referred to as functional equivalents of human GM-CSF, and may be such as variants and fragments of native human GM-CSF as described here below.

As used herein the expression "variant" refers to polypeptides or proteins which are homologous to the basic protein, which is suitably human GM-CSF, but which differ from the base sequence from which they are derived in that one or more amino acids within the sequence are substituted by other amino acids. Amino acid substitutions may be regarded as "conservative" where an amino acid is replaced with a different amino acid with broadly similar properties. Non-conservative substitutions are where amino acids are replaced with amino acids of a different type. Broadly speaking, fewer non-conservative substitutions will be possible without altering the biological activity of the polypeptide.

A person skilled in the art will know how to make and assess 'conservative' amino acid substitutions, by which one amino acid is substituted for another with one or more shared chemical and/or physical characteristics. Conservative amino acid substitutions are less likely to affect the functionality of the protein. Amino acids may be grouped according to shared characteristics. A conservative amino acid substitution is a substitution of one amino acid within a predetermined group of amino acids for another amino acid within the same group, wherein the amino acids within a predetermined groups exhibit similar or substantially similar characteristics. Within the meaning of the term "conservative amino acid substitution" as applied herein, one amino acid may be substituted for another within groups of amino acids characterised by having i) polar side chains (Asp, Glu, Lys, Arg, His, Asn, Gln, Ser, Thr, Tyr, and Cys,)
ii) non-polar side chains (Gly, Ala, Val, Leu, Ile, Phe, Trp, Pro, and Met)
iii) aliphatic side chains (Gly, Ala Val, Leu, Ile)
iv) cyclic side chains (Phe, Tyr, Trp, His, Pro)
v) aromatic side chains (Phe, Tyr, Trp)
vi) acidic side chains (Asp, Glu)
vii) basic side chains (Lys, Arg, His)
viii) amide side chains (Asn, Gln)
ix) hydroxy side chains (Ser, Thr)
x) sulphor-containing side chains (Cys, Met), and
xi) amino acids being monoamino-dicarboxylic acids or monoamino-monocarboxylic-monoamidocarboxylic acids (Asp, Glu, Asn, Gln).

A functional homologue within the scope of the present invention is a polypeptide that exhibits at least 50% sequence identity with human GM-CSF as identified by SEQ ID NO. 1, preferably at least 60%, 70% sequence identity preferably functional homologues have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with SEQ ID NO: 1.

Sequence identity can be calculated using a number of well-known algorithms and applying a number of different gap penalties. Any sequence alignment algorithm, such as but not limited to FASTA, BLAST, or GETSEQ may be used for searching homologues and calculating sequence identity. Moreover, when appropriate any commonly known substitution matrix, such as but not limited to PAM, BLOSSUM or PSSM matrices, may be applied with the search algorithm. For example, a PSSM (position specific scoring matrix) may be applied via the PSI-BLAST program. Moreover, sequence alignments may be performed using a range of penalties for gap opening and extension. For example, the BLAST algorithm may be used with a gap opening penalty in the range 5-12, and a gap extension penalty in the range 1-2.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino acid substitution from more than one group of conservative amino acids as defined herein above.

Aside from the twenty standard amino acids and two special amino acids, selenocysteine and pyrrolysine, there are a vast number of "nonstandard amino acids" which are not incorporated into protein in vivo. Examples of nonstandard amino acids include the sulfur-containing taurine and the neurotransmitters GABA and dopamine. Other examples are lanthionine, 2-Aminoisobutyric acid, and dehydroalanine. Further non-standard amino are ornithine and citrulline.

Non-standard amino acids are usually formed through modifications to standard amino acids. For example, taurine can be formed by the decarboxylation of cysteine, while dopamine is synthesized from tyrosine and hydroxyproline is made by a posttranslational modification of proline (common in collagen).

Both standard and non-standard amino acid residues described herein can be in the "D" or or "L" isomeric form.

It is contemplated that a functional equivalent according to the invention may comprise any amino acid including non-standard amino acids. In preferred embodiments a functional equivalent comprises only standard amino acids.

The standard and/or non-standard amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally-occurring amino acids. Several such analogs are known, including fluorophenylalanine, norleucine, azetidine-2-carboxylic acid, S-aminoethyl cysteine, 4-methyl tryptophan and the like.

Functional equivalents may further comprise chemical modifications such as ubiquitination, labeling (e.g., with radionuclides, various enzymes, etc.), pegylation (derivatization with polyethylene glycol), or by insertion (or substitution by chemical synthesis) of amino acids (amino acids) such as ornithine, which do not normally occur in human proteins.

In addition to the peptidyl compounds described herein, sterically similar compounds may be formulated to mimic the key portions of the peptide structure and that such compounds may also be used in the same manner as the peptides of the invention. This may be achieved by techniques of modelling and chemical designing known to those of skill in the art. For example, esterification and other alkylations may be employed to modify the amino terminus of, e.g., a di-arginine peptide backbone, to mimic a tetra peptide structure. It will be understood that all such sterically similar constructs fall within the scope of the present invention.

Peptides with N-terminal alkylations and C-terminal esterifications are also encompassed within the present invention. Functional equivalents also comprise glycosylated and covalent or aggregative conjugates formed with the same molecules, including dimers or unrelated chemical moieties. Such functional equivalents are prepared by linkage of functionalities to groups which are found in fragment including at any one or both of the N- and C-termini, by means known in the art.

The term "fragment thereof" may refer to any portion of the given amino acid sequence. Fragments may comprise more than one portion from within the full-length protein, joined together. Suitable fragments may be deletion or addition mutants. The addition of at least one amino acid may be an addition of from preferably 2 to 250 amino acids, such as from 10 to 20 amino acids, for example from 20 to 30 amino acids, such as from 40 to 50 amino acids. Fragments may include small regions from the protein or combinations of these.

Suitable fragments may be deletion or addition mutants. The addition or deletion of at least one amino acid may be an addition or deletion of from preferably 2 to 250 amino acids, such as from 10 to 20 amino acids, for example from 20 to 30 amino acids, such as from 40 to 50 amino acids. The deletion and/or the addition may—independently of one another—be a deletion and/or an addition within a sequence and/or at the end of a sequence.

Deletion mutants suitably comprise at least 20 or 40 consecutive amino acids and more, preferably at least 80 or 100 consecutive amino acids in length. Accordingly such a fragment may be a shorter sequence of the sequence as identified by SEQ ID NO: 1 comprising at least 20 consecutive amino acids, for example at least 30 consecutive amino acids, such as at least 40 consecutive amino acids, for example at least 50 consecutive amino acids, such as at least 60 consecutive amino acids, wherein said deletion mutant preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with SEQ ID NO: 1.

It is preferred that functional homologues of GM-CSF comprise at the most 500, more preferably at the most 400, even more preferably at the most 300, yet more preferably at the most 200, such as at the most 175, for example at the most 160, such as at the most 150 amino acids, for example at the most 144 amino acids.

The term "fragment thereof" may refer to any portion of the given amino acid sequence. Fragments may comprise more than one portion from within the full-length protein, joined together. Portions will suitably comprise at least 5 and preferably at least 10 consecutive amino acids from the basic sequence. They may include small regions from the protein or combinations of these.

There are two known variants of human GM-CSF; a T1151 substitution in variant and a I117T substitution in variant 2 (numbering as in SEQ ID NO: 2). Accordingly, in one embodiment of the invention functional homologues of GM-CSF comprises a sequence with high sequence identity to SEQ ID NO: 1 or any of the splice variants.

Analogs of GM-CSF are for example described in U.S. Pat. Nos. 5,229,496, 5,393,870, and 5,391,485 to Deeley, et al. Such analogues are also functional equivalents comprised within the present invention.

Recombinant Production

The present invention relates to the pulmonary administration, of granulocyte-macrophage colony stimulating factor (GM-CSF), or a functional homologue of thereof, however prepared, to treat a pulmonary NTM infection refractory to treatment, for example antibiotic treatment, in a subject in need thereof. GM-CSF can be produced in various ways, such as isolation from for example human or animal serum or from expression in cells, such as prokaryotic cells, yeast cells, insect cells, mammalian cells or in cell-free systems.

In one embodiment of the invention, GM-CSF is produced recombinantly by host cells.

Thus, in one aspect of the present invention, GM-CSF is produced by host cells comprising a first nucleic acid sequence encoding the GM-CSF operably associated with a second nucleic acid capable of directing expression in said host cells. The second nucleic acid sequence may thus comprise or even consist of a promoter that will direct the expression of protein of interest in said cells. A skilled person will be readily capable of identifying useful second nucleic acid sequence for use in a given host cell.

The process of producing recombinant GM-CSF in general comprises the steps of:

- providing a host cell
- preparing a gene expression construct comprising a first nucleic acid encoding GM-CSF operably linked to a second nucleic acid capable of directing expression of said protein of interest in the host cell
- transforming the host cell with the construct,
- cultivating the host cell, thereby obtaining expression of GM-CSF.

The recombinant GM-CSF thus produced may be isolated by any conventional method, such as any of the methods for protein isolation described herein below. The skilled person will be able to identify suitable protein isolation steps for purifying GM-CSF.

In one embodiment of the invention, the recombinantly produced GM-CSF is excreted by the host cells. When GM-CSF is excreted the process of producing a recombinant protein of interest may comprise the following steps:

- providing a host cell
- preparing a gene expression construct comprising a first nucleic acid encoding GM-CSF operably linked to a second nucleic acid capable of directing expression of said protein of interest in said host cell
- transforming said host cell with the construct,
- cultivating the host cell, thereby obtaining expression of GM-CSF and secretion of GM-CSF into the culture medium,
- thereby obtaining culture medium comprising GM-CSF.

The composition comprising GM-CSF and nucleic acids may thus in this embodiment of the invention be the culture medium or a composition prepared from the culture medium.

In another embodiment of the invention said composition is an extract prepared from animals, parts thereof or cells or an isolated fraction of such an extract.

In an embodiment of the invention, GM-CSF is recombinantly produced in vitro in host cells and is isolated from cell lysate, cell extract or from tissue culture supernatant. In a more preferred embodiment GM-CSF is produced by host cells that are modified in such a way that they express GM-CSF. In an even more preferred embodiment of the invention said host cells are transformed to produce and excrete GM-CSF.

Administration

Methods of intratracheal, intrabronchial or bronchio-alveolar administration include, but are not limited to, spraying, lavage, inhalation, flushing or instillation, using as fluid a physiologically acceptable composition in which GM-CSF have been dissolved. When used herein the terms "intratracheal, intrabronchial or intraalveolar administration" include all forms of such administration whereby GM-CSF is applied into the trachea, the bronchi or the alveoli, respectively, whether by the instillation of a solution of GM-CSF, by applying GM-CSF in a powder form, or by allowing GM-CSF to reach the relevant part of the airway by inhalation of GM-CSF as an aerosolized or nebulized solution or suspension or inhaled powder or gel, with or without added stabilizers or other excipients.

Methods of intrabronchial/alveolar administration include, but are not limited to, bronchoalveolar lavage (BAL) according to methods well known to those skilled in the art, using as a lavage fluid a physiologically acceptable composition in which GM-CSF been dissolved or indeed by any other effective form of intrabronchial administration including the use of inhaled powders containing GM-CSF in dry form, with or without excipients, or the direct application of GM-CSF, in solution or suspension or powder form during bronchoscopy. Methods for intratracheal administration include, but are not limited to, blind tracheal washing with a similar solution of dissolved GM-CSF or a GM-CSF suspension, or the inhalation of nebulized fluid droplets containing dissolved GM-CSF or a GM-CSF suspension obtained by use of any nebulizing apparatus adequate for this purpose.

In another embodiment, intratracheal, intrabronchial or intraalveolar administration does not include inhalation of the product but the instillation or application of a solution of GM-CSF or a powder or a gel containing GM-CSF into the trachea or lower airways.

Other preferred methods of administration may include using the following devices:

1. Pressurized nebulizers using compressed air/oxygen mixture
2. Ultrasonic nebulizers
3. Electronic micropump nebulizers (e.g. Aeroneb Professional Nebulizer)
4. Metered dose inhaler (MDI)
5. Dry powder inhaler systems (DPI)
6. Electronic vibrating mesh nebulizer.

The aerosol may be delivered by via a) facemasks or b) via endotracheal tubes in intubated patients during mechanical ventilation (devices 1, 2, 3, and 6). The devices 4, 5 and 6 can also be used by the patient without assistance provided that the patient is able to self-activate the aerosol device or nebulizer. The term "inhalator" may herein refer to any of the above devices, as well as any device allowing for delivery via inhalation.

Preferred concentrations for a solution comprising GM-CSF and/or functional homologues or variants of GM-CSF are in the range of 0.1 µg to 10000 µg active ingredient per ml solution. The suitable concentrations are often in the range of from 0.1 µg to 5000 µg per ml solution, such as in the range of from about 0.1 µg to 3000 µg per ml solution, and especially in the range of from about 0.1 µg to 1000 µg per ml solution, such as in the range of from about 0.1 µg to 250 µg per ml solution. Preferably, GM-CSF is delivered by an electronic vibrating mesh nebulizer delivering a GM-CSF solution at a range of between 100 and 500 µg per ml solution, such as between 150 and 400 µg per ml solution, such as between 200 and 300 µg per ml solution, such as about 250 µg per ml solution.

Pharmaceutical Composition

Pharmaceutical compositions or formulations for use in the present invention include GM-CSF or a functional homologue thereof combination with, preferably dissolved in, a pharmaceutically acceptable carrier, preferably an aqueous carrier or diluent, or carried to the lower airways as a pegylated preparation or as a liposomal or nanoparticle preparation administered as an aerosol via inhalation, or as a lavage fluid administered via a bronchoscope as a bronchoalveloar lavage or as a blind intratracheal wash or lavage. A variety of aqueous carriers may be used, including, but not limited to 0.9% saline, buffered saline, physiologically compatible buffers and the like. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution prior to administration In one embodiment a freeze-dried GM-CSF preparation may be pre-packaged for example in single dose units. In an even more preferred embodiment the single dose unit is adjusted to the patient.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

A suitable nebulizer solution of GM-CSF, for example molgramostim, may contain one or more excipients such as mannitol, polyethylene glycol 4000, Recombumin® Prime, disodium phosphate (anhydrous), citric acid (monohydrate) and water. In such solutions, the specific biological activity may be about $13\times10^6$ IU/mg across a number of drug substance batches, such as one drug substance batch, two drug substance batches, three drug substance batches, four drug substance batches, five drug substance batches, six drug substance batches, seven drug substance batches, eight drug substance batches, nine drug substance batches, ten drug substance batches or more. In some embodiments, the specific biological activity is between $1\times10^6$ IU/mg and $50\times10^6$ IU/mg, such as between $5\times10^6$ IU/mg and $40\times10^6$ IU/mg, such as between $7.5\times10^6$ IU/mg and $30\times10^6$ IU/mg, such as between $8\times10^6$ IU/mg and $25\times10^6$ IU/mg, such as between $9\times10^6$ IU/mg and $20\times10^6$ IU/mg, such as between $10\times10^6$ IU/mg and $18\times10^6$ IU/mg, such as between $11\times10^6$ IU/mg and $16\times10^6$ IU/mg, such as between $12\times10^6$ IU/mg and $14\times10^6$ IU/mg, such as $13\times10^6$ IU/mg.

The formulations may contain pharmaceutically acceptable carriers and excipients including microspheres, liposomes, microcapsules, nanoparticles or the like. Conventional liposomes are typically composed of phospholipids (neutral or negatively charged) and/or cholesterol. The liposomes are vesicular structures based on lipid bilayers surrounding aqueous compartments. They can vary in their physiochemical properties such as size, lipid composition, surface charge and number and fluidity of the phospholipids bilayers. The most frequently used lipid for liposome formation are: 1,2-Dilauroyl-sn-Glycero-3-Phosphocholine (DLPC), 1,2-Dimyristoyl-sn-Glycero-3-Phosphocholine (DMPC), 1,2-Dipalmitoyl-sn-Glycero-3-Phosphocholine (DPPC), 1,2-Distearoyl-sn-Glycero-3-Phosphocholine (DSPC), 1,2-Dioleoyl-sn-Glycero-3-Phosphocholine (DOPC), 1,2-Dimyristoyl-sn-Glycero-3-Phosphoethanolamine (DMPE), 1,2-Dipalmitoyl-sn-Glycero-3-Phosphoethanolamine (DPPE), 1,2-Dioleoyl-sn-Glycero-3-Phosphoethanolamine (DOPE), 1,2-Dimyristoyl-sn-Glycero-3-Phosphate (Monosodium Salt) (DMPA), 1,2-Dipalmitoyl-sn-Glycero-3-Phosphate (Monosodium Salt) (DPPA), 1,2-Dioleoyl-sn-Glycero-3-Phosphate (Monosodium Salt) (DOPA), 1,2-Dimyristoyl-sn-Glycero-3-[Phospho-rac-(1-glycerol)] (Sodium Salt) (DMPG), 1,2-Dipalmitoyl-sn-Glycero-3-[Phospho-rac-(1-glycerol)] (Sodium Salt) (DPPG), 1,2-Dioleoyl-sn-Glycero-3-[Phospho-rac-(1-glycerol)] (Sodium Salt) (DOPG), 1,2-Dimyristoyl-sn-Glycero-3-[Phospho-L-Serine] (Sodium Salt) (DMPS), 1,2-Dipalmitoyl-sn-Glycero-3-[Phospho-L-Serine) (Sodium Salt) (DPPS), 1,2-Dioleoyl-sn-Glycero-3-[Phospho-L-Serine] (Sodium Salt) (DOPS), 1,2-Dioleoyl-sn-Glycero-3-Phosphoethanolamine-N-(glutaryl) (Sodium Salt) and 1,1',2,2'-Tetramyristoyl Cardiolipin (Ammonium Salt). Formulations composed of DPPC in combination with other lipids or modifiers of liposomes are preferred e.g. in combination with cholesterol and/or phosphatidylcholine.

Long-circulating liposomes are characterized by their ability to extravasate at body sites where the permeability of the vascular wall is increased. The most popular way of producing long-circulating liposomes is to attach hydrophilic polymer polyethylene glycol (PEG) covalently to the outer surface of the liposome. Some of the preferred lipids are: 1,2-Dipalmitoyl-sn-Glycero-3-Phosphoethanolamine-N-[Methoxy(Polyethylene glycol)-2000] (Ammonium Salt), 1,2-Dipalmitoyl-sn-Glycero-3-Phosphoethanolamine-N-[Methoxy(Polyethylene glycol)-5000] (Ammonium Salt), 1,2-Dioleoyl-3-Trimethylammonium-Propane (Chloride Salt) (DOTAP).

Possible lipids applicable for liposomes are supplied by Avanti, Polar Lipids, Inc, Alabaster, AL Additionally, the liposome suspension may include lipid-protective agents which protect lipids against free-radical and lipid-peroxidative damage on storage. Lipophilic free-radical quenchers, such as alpha-tocopherol and water-soluble iron-specific chelators, such as ferrioxianine, are preferred.

A variety of methods are available for preparing liposomes, as described in, e.g., Szoka et al. (1980), U.S. Pat. Nos. 4,235,871, 4,501,728 and 4,837,028, all of which are incorporated herein by reference. Another method produces multi-lamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous solution of the targeted drug and the targeting component and allowed to hydrate, typically over a 15-60 minute period with agitation. The size distribution of the resulting multi-lamellar vesicles can be shifted toward smaller sizes by hydrating the lipids under more vigorous agitation conditions or by adding solubilizing detergents such as deoxycholate.

Micelles are formed by surfactants (molecules that contain a hydrophobic portion and one or more ionic or otherwise strongly hydrophilic groups) in aqueous solution.

Common surfactants well known to one of skill in the art can be used in the micelles of the present invention. Suitable surfactants include sodium laureate, sodium oleate, sodium lauryl sulfate, octaoxyethylene glycol monododecyl ether, octoxynol 9 and PLURONIC F-127 (Wyandotte Chemicals Corp.). Preferred surfactants are nonionic polyoxyethylene and polyoxypropylene detergents compatible with IV injection such as, TWEEN-80, PLURONIC F-68, n-octyl-beta-D-glucopyranoside, and the like. In addition, phospholipids, such as those described for use in the production of liposomes, may also be used for micelle formation.

In some cases, it will be advantageous to include a compound, which promotes delivery of the active substance to its target.

Dose

By "effective amount" of GM-CSF it is meant a dose, which, when administered via pulmonary administration, achieves a concentration in the subject's airways and/or lung parenchyma which allows treatment of a refractory NTM. The improvement may be observed already after one week, after two weeks, after three weeks, one month, after two months, after three months, after six months, after one year, or after eighteen months or more.

The preparations are administered in a manner compatible with the dosage formulation, and in such amount as will be therapeutically effective. The quantity to be administered depends on the subject to be treated, including, e.g. the weight and age of the subject, the disease to be treated and the stage of disease. Suitable dosage ranges are normally of the order of several hundred µg active ingredient per administration with a preferred range of from about 100 to 1000 µg per administration. Doses expected to provide an effective amount of GM-CSF comprise GM-CSF are often in the range of between 100 and 1000 µg, such as between 100 and 900 µg, such as between 100 and 800 µg, such as between 125 and 700 µg, such as between 150 and 600 µg, such as between 200 and 400 µg, such as between 250 and 350 µg, such as 250 µg or 300 µg administered via pulmonary administration. In one embodiment, pulmonary administration is by inhalation. Administration may occur once or twice daily, preferably the administration occurs once daily. Administration may occur once or twice daily every week, or administration may occur once or twice daily every second week.

Using monomeric forms of the compounds, the suitable dosages are often in the range of from 100 and 1000 µg, such as between 100 and 900 µg, such as between 200 and 800 µg, such as between 300 and 700 µg, such as between 400 and 600 µg, such as 500 µg per day, when based on monomeric forms having a sequence identical to sequence ID NO: 1, for functional homologues and fragments the dose is calculated based on the molecular weight of the monomeric form to the molecular weight of the homologues or fragments.

GM-CSF may be administered at a dosage of between 100 and 500 µg, such as between 125 and 450 µg, such as between 150 and 400 µg, such as between 175 and 375 µg, such as between 200 and 350 µg, such as between 225 and 325 µg, such as between 250 and 325 µg, such as between 275 and 325 µg, such as 250 µg or 300 µg.

Duration of dosing will typically range from 1 day to about 18 months, such as from one week to about 16 months, such as from two weeks to about 14 months, such as from one month to about 12 months, such as from 6 weeks to about 10 months, such as from 2 months to about 8 months, such as from 3 months to about 6 months, such as 3, 4, 5 or 6 months. Any of these durations can be used with any of the above defined dosages. In some cases it may be advantageous to continue administration for more than 18 months.

Suitable frequencies of administration are once per day, every second day, every third day, three times a week, twice a week or once a week. Any of these frequencies can be used with any of the dosages defined above.

In some embodiments, the GM-CSF is administered until the subject is no longer showing signs of NTM infections. GM-CSF may thus be discontinued after one or more of the following has been observed in samples originating from the subject:

sputum cultures negative for NTM;
negative NTM staining;
quantitative PCR indicating absence of NTM in cultures;
bronchial lavage cultures negative for NTM;
lung biopsy showing absence of NTM.

Medical Packaging

The compounds used in the invention may be administered alone or in combination with pharmaceutically acceptable carriers or excipients, in either single or multiple doses. The formulations may conveniently be presented in unit dosage form by methods known to those skilled in the art.

It is preferred that the compounds according to the invention are provided in a kit. Such a kit typically contains an active compound in dosage forms for administration. A dosage form contains a sufficient amount of active compound such that a desirable effect can be obtained when administered to a subject.

Thus, it is preferred that the medical packaging comprises an amount of dosage units corresponding to the relevant dosage regimen. Accordingly, in one embodiment, the medical packaging comprises a pharmaceutical composition comprising a compound as defined above or a pharmaceutically acceptable salt thereof and pharmaceutically acceptable carriers, vehicles and/or excipients, said packaging comprising from 1 to 7 dosage units, thereby having dosage units for one or more days, or from 7 to 28 dosage units, or multiples thereof, thereby having dosage units for one week of administration or several weeks of administration.

The dosage units can be as defined above. The medical packaging may be in any suitable form for intratracheal, intrabronchial or intraalveolar administration. In a preferred embodiment the packaging is in the form of a vial, ampule, tube, blister pack, cartridge or capsule.

When the medical packaging comprises more than one dosage unit, it is preferred that the medical packaging is provided with a mechanism to adjust each administration to one dosage unit only.

Preferably, a kit contains instructions indicating the use of the dosage form to achieve a desirable affect and the amount of dosage form to be taken over a specified time period. Accordingly, in one embodiment the medical packaging comprises instructions for administering the pharmaceutical composition.

In some embodiments, a freeze-dried GM-CSF preparation may be pre-packaged for example in single dose units. In an even more preferred embodiment the single dose unit is adjusted to the patient.

In some embodiments, the dosage unit of GM-CSF is provided as a solution in a glass vial, which is suitable for use with a nebuliser such as an electric vibrating mesh nebuliser. Several glass vials may be gathered in a container.

An exemplary suitable volume of the solution contained within a glass vial is 1.2 mL.

EXAMPLES

Example 1

Study A: Inhaled GM-CSF in Addition to Antibiotic Therapy in Patients Refractory to Current Therapy Inclusion Criteria:

Patients who have continued culture of NTM in their sputum despite 6-months of standard (3-drug) antibiotic therapy and will continue on antibiotic therapy.

Case 1: A 65-year-old female with history of bronchiectasis for 6 years complicated by multiple infections, including *Mycobacterium intracellulare* and *M. abscessus*. Her disease is characterized by pulmonary symptoms, cavitary and nodular findings on chest X-ray and multifocal bronchiectasis on HRCT scan. Fifteen months prior to study inclusion she was diagnosed with *M. intracellulare* and received treatment with the antibiotics ethambutol and rifampicin, and 10 months later azithromycin was added. At inclusion in study she started daily treatment with 300 μg inhaled GM-CSF (molgramostim) in addition to the ongoing triple-combination antimycobacterial treatment.

At screening her sputum smear was 1+ positive for acid fast bacilli (AFB) and culture showed growth of *M. intracellulare*. At baseline sputum smear showed occasional AFB but the isolate failed to grow on culture.

After 4, 8, 12 and 16 and 20 weeks of treatment sputum smear was negative. There was no growth of NTM after 4, 8 and 12 weeks; cultures from weeks 16 and 20 are in process.

After 12 weeks of treatment, the patient reported an improvement in tiredness from 5 to 1 on a 10-cm Visual Analogue Scale (VAS), which was sustained through week 16.

Example 2

Study B: Inhaled GM-CSF as Mono-Therapy in Patients with Refractory NTM Disease Resistant to Antibiotic Therapy Inclusion Criteria:

Patients who have continued culture of NTM in their sputum despite at least 6-months of standard (3-drug) antibiotic therapy in the past 3-years and they or their clinicians do not wish to recommence antibiotic therapy.

Case 2: 10 year old female had a 3.5 year history of persistent *M. abscessus* colonization. The subject was homozygous for the ΔF508 mutation within the CTFR (cystic fibrosis transmembrane conductance regulator) gene, known to be responsible for cystic fibrosis.

Nodular infiltrates and clinical decline prompted antibiotic treatment (intravenous amikacin, cefoxitin and oral linezolid) for 2 years. Cefoxitin was discontinued after 1 month due to rash, despite attempting cefoxitin desensitization. Ototoxicity due to amikacin was noted after 4 months; intravenous amikacin was then replaced with aerosolized amikacin. Despite linezolid (i.v.) and amikacin (inhaled) therapy pulmonary function and body mass declined and bronchoalveolar lavage (BAL) specimens returned to smear positive for many organisms and heavy growth of *M. abscessus*. The organism exhibited intermediate sensitivity to amikacin and cefoxitin, while being sensitive to linezolid.

Aerosolized GM-CSF (Sargramostim, Genenzyme, Cambridge, MA, 250 μg twice daily diluted in 2 $cm^3$ saline) was added and administered on alternate weeks via a nebulizer. There was clinical improvement as well as a decrease in radiologic opacities within areas of extensive varicoid and cystic bronchiectasis. Clinical improvement and stability were noted. GM-CSF was continued and antibiotics were discontinued after 3 months. After remaining off antibiotics for 3 months a decision was made to recombine aerosolized GM-CSF with linezolid (i.v.) and amikacin (inhaled). After 4 months of combined therapy both acid-fast bacillus (AFB) smear and cultures became negative. The patient remains on inhaled GM-CSF therapy alone.

TABLE 1

| Case (No.) | GM-CSF Duration of Therapy (weeks) | FVC (% predicted) | $FEV_1$ (% predicted) |
| --- | --- | --- | --- |
| 1 | 0 | 62.5 | 64.7 |
|  | 16 | 73.0 | 75.0 |
|  | 90 | 79.0 | 78.0 |

GM-CSF: granulocyte-macrophage-colony stimulating factor.
FVC: forced vital capacity.
$FEV_1$: forced expiratory volume in 1 second.
BAL: bronchoalveolar lavage.
AFB: acid fast bacilli.

Case 3: 25 year old ΔF508 homozygous male with cystic fibrosis-related diabetes mellitus had a 13 year history of persistent *M. abscessus*. New radiologic nodular infiltrates, loss of weight and fall in lung function were noted despite ongoing use of lumicaftor/ivacaftor. AFB smear showed many organisms.

Administration of aerosolized GM-CSF 250 μg twice daily every second week (one week on/one week off) was initiated without antibiotic therapy. Clinical improvement was noted without observing toxicity. After 6 months of GM-CSF sputum smears became negative and culture burden decreased to 1 colony per plate. Subsequently, culture burden became negative.

TABLE 2

| Case (No.) | GM-CSF Duration of Therapy (weeks) | FVC (% predicted) | $FEV_1$ (% predicted) |
| --- | --- | --- | --- |
| 2 | 0 | 72.5 | 55.2 |
|  | 9 | 80.9 | 60.7 |
|  | 26 | 81.6 | 63.9 |

GM-CSF: granulocyte-macrophage-colony stimulating factor.
FVC: forced vital capacity.
$FEV_1$: forced expiratory volume in 1 second.
BAL: bronchoalveolar lavage.
AFB: acid fast bacilli.

REFERENCES

Altemeier W A, Sinclair S E. Hyperoxia in the intensive care unit: why more is not always better. Curr Opin Crit Care. 2007 February; 13(1):73-8.

Baleeiro C E, Christensen P J, Morris S B, Mendez M P, Wilcoxen S E, Paine R. GM-CSF and the impaired pulmonary innate immune response following hyperoxic stress. Am J Physiol Lung Cell Mol Physiol. 2006 December; 291(6):L1246-55.

Chen G H, Olszewski M A, McDonald R A, Wells J C, Paine R 3rd, Huffnagle G B, Toews G B. Role of granulocyte macrophage colony-stimulating factor in host defense against pulmonary *Cryptococcus neoformans* infection during murine allergic bronchopulmonary mycosis. Am J Pathol. 2007 March; 170(3):1028-40

Griffith D E, Aksamit T, Brown-Elliott B A, et al. An Official ATS/IDSA Statement: Diagnosis, Treatment, and Prevention of Nontuberculous Mycobacterial Diseases. Am J Respir Crit Care Med. 2007; 175(4):367-416

Quittner A L, O'Donnell A E, Salathe M A, et al. Quality of Life Questionnaire-Bronchiectasis: final psychometric analyses and determination of minimal important difference scores. Thorax. 2015; 70(1):12-20

Szoka et al., Comparative properties and methods of preparation of lipid vesicles (liposomes). Ann. Rev. Biophys. Bioeng. 9:467 (1980)

Trapnell B C and Whitsett J A. GM-CSF regulates pulmonary surfactant homeostasis and alveolar macrophage-mediated innate host defense. Annu. Rev. Physiol. 2002. 64:775-802

U.S. Pat. No. 4,235,871
U.S. Pat. No. 4,501,728
U.S. Pat. No. 4,837,028,
U.S. Pat. No. 5,391,485
U.S. Pat. No. 5,393,870
U.S. Pat. Nos 5,229,496
Wong et al., Science Vol. 228, pp. 810-815 (1985)

Zobywalski A, Javorovic M, Frankenberger B, Pohla H, Kremmer E, Bigalke I, Schendel DJ. Generation of clinical grade dendritic cells with capacity to produce biologically active IL-12p70. J Transl Med. 2007 Apr. 12; 5:18

The invention claimed is:

1. A method of treating a pulmonary non-tuberculous mycobacterium (NTM) infection in a subject having a pulmonary NTM infection refractory to antibiotic treatment, the method comprising administering to the subject via pulmonary administration an effective amount of a granulocyte-macrophage colony stimulating factor (GM-CSF) in the range of 200 µg to 400 µg once or twice daily, wherein the GM-CSF is administered to the subject every week or every alternate week for at least 6 months until a sputum sample originating from the subject shows an absence of NTM, thereby treating the subject.

2. The method of claim 1, wherein the GM-CSF is administered at a dosage 250 µg.

3. The method of claim 1, wherein the GM-CSF is administered twice daily.

4. The method of claim 1, wherein the NTM is a photochromogen, a non-chromogen, a scotochromogen, or a rapid grower.

5. The method of claim 1, wherein the NTM is *Mycobacterium kansasii, Mycobacterium simiae, Mycobacterium marinum, Mycobacterium scrofulaceum, Mycobacterium szulgai, Mycobacterium avium complex* (MAC), *Mycobacterium ulcerans, Mycobacterium xenopi, Mycobacterium malmoense, Mycobacterium terrae, Mycobacterium haemophilum, Mycobacterium genavense, Mycobacterium chelonae, Mycobacterium abscessus, Mycobacterium fortuitum, Mycobacterium peregrinum, Mycobacterium smegmatis, Mycobacterium intracellulare,* or *Mycobacterium flavescens.*

6. The method of claim 1, wherein the NTM is selected from MAC, *Mycobacterium abscessus, 44, Mycobacterium fortuitum,* and *Mycobacterium kansasii.*

7. The method of claim 1, wherein the GM-CSF is administered by intratracheal, intrabronchial, or intraalveolar administration.

8. The method of claim 1, wherein the subject is administered a nebulized solution of the GM-CSF or a suspension of the GM-CSF.

9. The method of claim 1, wherein the subject is administered a nebulized aerosol of the GM-CSF or an inhaled powder form of the GM-CSF.

10. The method of claim 1, wherein the subject is a human.

11. The method of claim 1, wherein the subject has previously suffered from at least one NTM infection.

12. The method of claim 1, wherein the pulmonary NTM infection is refractory to treatment with one antibiotic.

13. The method of claim 1, wherein the pulmonary NTM infection is refractory to treatment with one antibiotic in combination with rifamycin or an injectable aminoglycoside.

14. The method of claim 12, wherein the antibiotic is selected from azithromycin, rifampin, isoniazid, ethambutol, ethionamide, streptomycin, clarithromycin, ethambutol, rifampicin, azithromycin, clofazimine, linezolid, amikacin, cefoxitin, pyrazinamide, isoniazid, and combinations thereof.

15. The method of claim 1, wherein the subject has been diagnosed by multiple sputum NTM cultures, NTM staining, quantitative PCR, bronchial lavage NTM culture, or lung biopsy.

16. The method of claim 1, wherein the subject has received an antibiotic treatment for at least one month and a sputum sample originating from the subject still has NTM.

17. The method of claim 1, wherein the GM-CSF is administered concomitantly with an antibiotic.

18. The method of claim 1, wherein the GM-CSF comprises a polypeptide having at least 90% sequence identity with SEQ ID NO: 1.

19. The method of claim 1, wherein the GM-CSF comprises a polypeptide of SEQ ID NO: 1.

20. The method of claim 1, wherein the GM-CSF is Molgramostim, Regramostim, or Sargramostim.

21. A method of treating a pulmonary non-tuberculous mycobacterium (NTM) infection in a subject having a pulmonary NTM infection refractory to antibiotic treatment, the method comprising:
  administering to the subject once or twice daily, via pulmonary administration, between 200 µg and 400 µg of a granulocyte-macrophage colony stimulating factor (GM-CSF) comprising a polypeptide having at least 90% sequence identity with SEQ ID NO:1, wherein the GM-CSF is administered to the subject every week or every alternate week for at least 6 months until a sputum sample originating from the subject shows an absence of NTM, thereby treating the subject; and
  wherein the NTM infection is *Mycobacterium abscessus* infection, a *Mycobacterium intracellulare* infection, or a *Mycobacterium abscessus* infection and a *Mycobacterium intracellulare* infection.

22. The method of claim 21, wherein the GM-CSF is administered twice daily.

23. The method of claim 21, wherein the GM-CSF is administered at a dosage of 250 µg.

* * * * *

UNITED STATES PATENT AND TRADEMARK OFFICE
CERTIFICATE OF CORRECTION

PATENT NO. : 11,938,169 B2
APPLICATION NO. : 16/755178
DATED : March 26, 2024
INVENTOR(S) : Inge Tarnow, Cecilia Ganslandt and Mark E. Wylam It is certified that error appears in the above-identified patent and that said Letters Patent is hereby corrected as shown below:

In the Claims

Under Column No. 21, Line 49, replace:
"from MAC, Mycobacterium abscessus, 44, Mycobacterium"
With:
--from MAC, Mycobacterium abscessus, Mycobacterium--

Under Column No. 22, Line 56, replace:
"wherein the NTM infection is Mycobacterium abscessus"
With:
--wherein the NTM infection is a Mycobacterium abscessus--

Signed and Sealed this
Twenty-third Day of July, 2024

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 127
<212> TYPE: PRT
<213> ORGANISM: Homo sapiens

<400> SEQUENCE: 1

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 2
<211> LENGTH: 144
<212> TYPE: PRT
<213> ORGANISM: Homo sapiens
<220> FEATURE:
<221> NAME/KEY: MISC_FEATURE
<222> LOCATION: (1)..(17)
<223> OTHER INFORMATION: Signal peptide

<400> SEQUENCE: 2

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60
```

-continued

```
Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140
```